United States Patent [19]

Hammond

[11] Patent Number: 4,997,814

[45] Date of Patent: Mar. 5, 1991

[54] PHARMACEUTICAL COMPOSITIONS AND USE THEREOF IN TREATING INFLAMMATION

[75] Inventor: Geoffrey L. Hammond, Lambeth, Canada

[73] Assignee: Allelix Biopharmaceuticals, Inc., Mississauga, Canada

[21] Appl. No.: 204,356

[22] Filed: Jun. 9, 1988

[51] Int. Cl.$^5$ .............................................. A61K 37/04
[52] U.S. Cl. ........................................ 514/8; 514/21; 514/179; 530/386
[58] Field of Search ........................... 514/21, 8, 179; 530/386

[56] References Cited

PUBLICATIONS

David–Gwynne, Corticosteroids, p. 446.
Feldman et al, CA, vol. 92, 1980, 69859d.
Savu et al.; Corticosterone Binding Globulin: An Acute Phase, "Negative", Protein in the Rat; FEBS Letters (1980); 113: 102–106.
Pugeat et al.; Transport of Steroid Hormones: Interaction of 70 Drugs with Testosterone-Binding Globulin and Cortico-Steroid-Binding Globulin in Human Plasma; Chemical Abstracts (1981); vol. 95.
Pemberton, "Hormone Binding Globulins Undergo Serpin Conformational Change in Inflammation", Nature, vol. 336, Nov. 1988.
Mickelson, et al., *Biochemistry*, "d–Protein Interactions, Human Corticosteroid Binding Globulin: Physicochemical Properties and Binding Specificity", vol. 20, pp. 6211–6218 (1981).
W. Rosner, *Journal of Steroid Biochemistry*, "Recent Studies on the Binding of Cortisol in Serum", vol. 3, pp. 531–542 (1972).
Robinson, et al., *J. Endocr.*, "A Solid–Phase Radioimmunoassay for Human Corticosteroid Binding Globulin", vol. 104, pp. 259–267 (1985).
Martindale, *The Extra Pharmacopoeia*, "Corticosteroids", pp. 446–485 (1982).
Fernlund et al., *J. Steroid Biochem.*, "A Simple Two-Step Procedure for the Simultaneous Isolation of Corticosteroid Binding Globulin and Sex Hormone Binding Globulin from Serum by Chromatography on Cortisol-Sepharose and Phenyl-Sepharose", vol. 14, pp. 545–552 (1981).
Hammond, et al, *Proc. Natl. Acad. Sci. USA*, "Primary Structure of Human Corticosteroid Binding Globulin, Deduced from Hepatic and Pulmonary cDNAs, Exhibits Homology with Serine Protease Inhibitors", vol. 84, pp. 5153–5157 (1987).
Hammond, et al., *Clinical Chimica Acta*, "A Versatile Method for the Determination of Serum Cortisol Binding Globulin and Sex Hormone Binding Globulin Binding Capacities", vol. 132, pp. 101–110 (1983).
Brien, *Clinical Endocrinology*, "Human Corticosteroid Binding Globulin", vol. 14, pp. 193–212 (1981).

Primary Examiner—Howard E. Schain
Assistant Examiner—Choon P. Koh
Attorney, Agent, or Firm—Foley & Lardner, Schwartz, Jeffery, Schwaab, Mack, Blumenthal & Evans

[57] ABSTRACT

Inflammation in mammals is treated by administering anti-inflammatory agent complexed with corticosteroid binding globulin (CBG).

37 Claims, No Drawings

PHARMACEUTICAL COMPOSITIONS AND USE THEREOF IN TREATING INFLAMMATION

FIELD OF THE INVENTION

This invention relates to anti-inflammatory agents such as glucocorticoids and their use in treating inflammation.

BACKGROUND TO THE INVENTION

Glucocorticoids are steroid hormones, many of which are potent anti-inflammatory agents. Their physiological effects are not limited to their anti-inflammatory properties, however, nor are their effects restricted specifically to inflamed tissue. Protein, lipid and carbohydrate metabolism can be altered adversely and electrolyte balance can be disturbed particularly when large or repeated therapeutic doses of the anti-inflammatory glucocorticoids are administered.

Certain recently developed synthetic glucocorticoids show promise as therapeutic alternatives to the natural anti-inflammatory glucocorticoids such as cortisone, cortisol and corticosterone. The synthetic analogues, which include dexamethasone and betamethasone, exhibit reduced effects on electrolyte balance and tend therefore to elicit fewer adverse side effects. In many instances, they also exhibit greater potency as anti-inflammatory agents relative to their natural counterparts, presumably owing to their reduced binding affinity for the plasma protein known as corticosteroid binding globulin (CBG). It has been reported that natural glucocorticoids become biologically inactivated upon binding with CBG in the circulation whereas many synthetic glucocorticoids do not bind and thus remain active (see Mickelson et al., *Biochemistry* 1981, 20, 6211–6218 where binding affinities for some natural and synthetic glucocorticoids relative to CBG are tabled). The capacity of synthetic glucocorticoids to escape CBG-binding and thus to remain free and biologically active following administration is presumed to be at least partly responsible for their enhanced anti-inflammatory properties in vivo.

Apart from the numerous physiological effects exerted by glucocorticoids, their use in treating inflammation is further complicated by their ability to affect a broad range of tissues, whether inflamed or healthy. Because so many tissues are responsive to corticosteroids, they are rarely administered systemically unless inflammation is particularly severe or life threatening.

SUMMARY OF THE INVENTION

It is therefore an object of the present invention to provide a strategy useful therapeutically for localizing the effects of anti-inflammatory agents, such as the glucocorticoids, predominantly to a site of inflammation.

In accomplishing this object, there is provided, in accordance with one aspect of the invention, a pharmaceutical composition useful in treating inflammation in a mammal which comprises CBG, an anti-inflammatory agent which binds therewith, and a pharmaceutically acceptable carrier. Any anti-inflammatory agent which binds with appropriate affinity to CBG may be used in the present composition. Preferably, the anti-inflammatory agent is present in an amount sufficient to bind substantially all of the CBG present in the composition. In one preferred embodiment of the invention, the anti-inflammatory agent is a glucocorticoid. Generally, the amount of anti-inflammatory agent required in the present composition is less than that required in the absence of CBG since, as will be explained, CBG is capable of localizing the effects of the anti-inflammatory agent to an inflammation site.

In accordance with another aspect of the invention, there is provided a method for treating inflammation in a mammal which comprises administering thereto a pharmaceutical composition comprising CBG-bound anti-inflammatory agent.

DETAILED DESCRIPTION OF THE INVENTION

It has now been found that the binding affinity of CBG for such anti-inflammatory agents as the glucocorticoids can be exploited to improve upon their therapeutic effectiveness as anti-inflammatory agents even though such agents are rendered biologically inactive when bound by CBG. More particularly, it has been found that CBG-bound glucocorticoids can be released from CBG at local sites of inflammation by the action of leukocyte elastase, an enzyme which is prevalent at sites of inflammation. Leukocyte elastase specifically cleaves the CBG component of the glucocorticoid: CBG complex, allowing glucocorticoid to dissociate from CBG and exert its anti-inflammatory action directly at the inflammation site. Accordingly, administration of glucocorticoid in CBG-bound form is an effective means for localizing glucocorticoid effects to those tissues or sites at which inflammation is active, thus reducing the indiscriminate stimulation of other tissues by glucocorticoids which results in undesirable side effects. Similarly, any anti-inflammatory agent which binds with CBG can be targetted for release specifically at an inflammation site by administering that particular agent in CBG-bound form.

That CBG is cleaved specifically by leukocyte elastase, a serine protease released locally by neutrophils at sites of inflammation, is particularly remarkable. First, the region that contains the proposed elastase binding site on another elastase substrate, $\alpha_1$-antitrypsin, is not well conserved when compared with CBG. Moreover, again by analogy with $\alpha_1$-antitrypsin, the putative elastase cleavage site on CBG involves a neighboring glycosylation site which is utilized in the CBG molecule, and is not involved in $\alpha_1$-antitrypsin. Yet, the experimental data herein provided demonstrates clearly that CBG is indeed cleaved by leukocyte elastase, at a site which is very close to that on the oxidized $\alpha_1$-antitrypsin molecule which is cleaved by macrophage elastase, and shows also that when cleaved by elastase, CBG loses steroid binding activity.

In accordance with the invention, anti-inflammatory agents which bind with CBG are administered in CBG-bound form to treat inflammation in mammals. It should be appreciated that the binding of a particular anti-inflammatory and CBG is mediated by the affinity of one molecule for the other and not through a physical link such as a covalent bond or chemical linking agent. The degree of affinity between CBG and the selected anti-inflammatory agent should be sufficient to enable CBG and the agent to remain in association following administration thereof to the mammal to be treated, and allow the corticosteroid to dissociate following elastase-induced cleavage of CBG at an inflammation site. To identify those anti-inflammatory agents suitable for use in the present invention, one simply determines whether CBG is capable of binding with a selected anti-inflammatory agent. In general, an anti-inflammatory agent having an affinity constant for CBG within the range from 0.1 to 10 nanomolar at about 4° C. and physiological pH is suitable for use with CBG according to the present invention. A protocol for screening anti-inflammatory agents for suitability in the present context is described by Mickelson et al., supra, incorporated herein by reference, which allows the binding affinity of a selected steroid for CBG to be compared with the affinity of CBG for one of its natural ligands, cortisol. Any anti-inflammatory agent having CBG binding affinity which approximates that of cortisol is suitable for use in accordance with the present invention. Mickelson et al., supra, also identify some criteria useful in predicting whether a particular steroid will be capable of binding adequately with CBG such as the presence of a 3-oxo group and the absence of an 11 α-hydroxy group on the steroid. While these criteria can be useful in determining binding affinity of steroid for CBG, it should be understood that the determinative measure of suitability of anti-inflammatory agent, whether steroidal in structure or not, is stability of the agent in CBG-bound form under the conditions noted above.

Specific anti-inflammatory agents useful herein include corticosteroids having glucocorticoid activity such as cortisol and other natural corticosteroids exhibiting anti-inflammatory properties such as corticosterone and cortisone. Synthetic glucocorticoids which exhibit reduced adverse effects on electrolyte balance, such as prednisolone and methylprednisolone are particularly suitable although, by intentional design, most other of the currently available synthetic glucocorticoids have an inappropriately low binding affinity for CBG. Nevertheless, synthetic corticosteroids developed subsequently or natural corticosteroids discovered hereafter are useful provided, of course, that they exhibit the appropriate level of anti-inflammatory activity and an appropriate CBG binding affinity, preferably a binding affinity for CBG which approximates that of cortisol (about 0.7 nanomolar at 4° C., physiological pH, as measured using the protocol described by Mickelson et al., supra).

The anti-inflammatory agent used in the pharmaceutical compositions of the invention should be of pharmaceutical grade. Whereas acid- and base-addition glucocorticoid salts are commonly employed in prior art compositions to enhance solubility of the glucocorticoid, in injectable solutions for example, salt forms of the selected glucocorticoid are not required in the present compositions although they may be used, if desired. When complexed with CBG, glucocorticoids are sufficiently soluble in solution in the amounts useful to treat inflammation, although solubilizers standard in the protein formulation art, such as mannitol, may be used.

CBG useful in the composition of the invention is now a well characterized protein, having been identified in human plasma over thirty years ago. It has since been identified in virtually every vertebrate species examined and has been isolated from numerous mammalian species including rabbit, guinea pig, rodent, humans and others. Techniques for isolating CBG from serum are now well known in the art. The most practical and efficient of these techniques involve the use of affinity columns in which the immobilized ligand is either a glucocorticoid or a derivative thereof which binds with high affinity to CBG. The preparation of such a column in which a cortisol derivative is cross-linked on Sepharose and its use in isolating CBG are described by Rosner in *J. Steroid Biochem*, 1972, 3, 531–542. An improved method for purifying human CBG from pregnancy serum, in which CBG levels are about 2-fold higher than normal serum, is described by Robinson et al in *J. Endocr.* (1985) 104, 259–267, incorporated herein by reference. The procedure entails applying serum to a column in which the ligand is a corticosterone derivative, collecting the CBG-containing eluate and then subjecting the eluate to successive purification steps such as gel electrophoresis and including a step in which contaminating albumin is removed.

Antibodies to CBG have also now been prepared (see Robinson et al., supra) and may also be employed to isolate CBG from serum.

In general, provided that the CBG used in the composition has the appropriate binding affinity for the selected glucocorticoid and is susceptible to cleavage by elastase, such CBG is suitable. It is conceivable that elastase endogenous in the mammalian species to be treated may have some specificity for the CBG native to that species. Given the importance of CBG cleavage by elastase in the present context, it is recommended that the administered composition comprises CBG native to the mammalian species being treated. For example, human CBG is preferably used in compositions administered to treat inflammation in humans and equine CBG is used when horses are to be treated.

To prepare compositions of the invention, the selected anti-inflammatory agent and CBG are simply admixed in solution, such as physiological saline, at pH 7.5, with agitation to generate the required complexes. Formation of CBG: anti-inflammatory agent complexes can be facilitated by incubating at physiological temperature and pH. It is important, when CBG-bound glucocorticoids are prepared to maintain pH above 6 because the affinity of CBG for glucocorticoid is reduced below pH 6. It is desirable, in order to achieve the maximum localizing effect of CBG, that the CBG in the administered composition is saturated with glucocorticoid i.e. the molar ratio of glucocorticoid bound to CBG in the composition is substantially 1:1. To accomplish this, it is preferred to use a molar excess of glucocorticoid such as a molar ratio of 2:1 (glucocorticoid:CBG) when generating the complexed material. Unbound glucocorticoid may remain with the complexed material, if desired.

To formulate CBG-bound glucocorticoid for administration, any of the conventional pharmaceutically acceptable carriers may be used, selection of which depends on the intended mode of administration and is dicated to some extent by the proteinaceous nature of the complexes. Injectable solutions may be prepared using well known liquid vehicles such as buffered saline and physiological saline. Compositions for topical application may be prepared as creams, lotions or ointments using an appropriate base such as triglycerides. Surface active agents may also be used as may preservatives to prevent microbial growth over prolonged storage periods. Aerosol inhalable formulations of CBG-bound glucocorticoid may also be prepared using propellant and an appropriate liquid vehicle.

The compositions of the invention are useful in pharmaceutical and in veterinary applications to treat a variety of conditions involving inflammation. It will be appreciated that the compositions are particularly better adapted for systemic administration than known compositions comprising free anti-inflammatory agent since CBG-binding thereof is capable, by the limiting of therapeutic action to an inflammation site, of reducing the potential for adverse side effects elsewhere in the body. Because of the effect which CBG has on controlling release of glucocorticoid, for example, it may be used in the present compositions in lower amounts relative to compositions of glucocorticoid per se, to elicit an anti-inflammatory response. When administered systemically as an injectable solution, formulations will comprise glucocorticoid (as CBG-bound glucocorticoid) in a molar range of 5-500 μM. To determine appropriate unit doses for treating a specific medical conditions with a particular anti-inflammatory agent, reference may be made to product monographs or more generally to Pharmacopoeias, such as Martindale, *The Extra Pharmacopoeia* Ed, J. E. F. Reynolds, The Pharmaceutical Press, London, 1982 (see particularly pp 446–485).

The compositions of the invention are useful to treat the same inflammation-related medical conditions or disorders as are treatable by the anti-inflammatory agents per se. In this connection, reference may be made to *The Extra Pharmacopoeia* cited above and incorporated herein by reference. For example, administration systemically of CBG-bound anti-inflammatory agent will be useful to treat blood disorders including autoimmune haemolytic anemia, idiopathic thrombocytopenic purpura, arthritis, septicemia etc. Local injection may be appropriate to treat collagen and rheumatoid disorders as well as certain connective tissue disorders. In cream, ointment or lotion form, the compositions may be applied to treat inflammation active at exposed areas of the skin. Topical administration of the compositions may be applied to open wounds to reduce inflammation. The administration of aerosols is appropriate for treating adult respiratory distress syndrome, respiratory ailments such as steroid dependent asthma and interstital lung disease. In general, administration of the compositions of the invention will be useful to reduce inflammation in areas where the CBG-corticosteroid complexes can become exposed, following administration, to the action of elastase.

DEMONSTRATION THAT LEUCOCYTE ELASTASE CLEAVES CBG

Human CBG was purified by affinity chromatography and Blue Sepharose chromatography, as previously described (Robinson et al., (1985) J. Endocrinol. 104:250). To evaluate the relationship of CBG to serine proteases, approximately 1 μg pure CBG was incubated (5 min at 37° C.) in 30 mM Tris, pH 7.5 (or pH optimal appropriate for the different serine proteases), with 20 ng human leucocyte elastase (Elastin Products Company, Inc), cathepsin G (EPC), thrombin (Boehringer Mannheim Canada) or plasmin (BMC). The reaction was terminated by boiling in 5 μl SDS-PAGE loading buffer, and then subjected to electrophoresis on a 12%-SDS polyacrylamide gel. After the gel was stained with Coomasie Blue, it was apparent that, under the experimental conditions, a clear ~5 kDa reduction in the apparent $M_r$ of human CBG occurred only after incubation with elastase.

In order to determine the site of cleavage, CBG and elastase were again incubated under the same conditions. The reaction was "snap frozen" and stored at −70° C. until subjected to amino-terminal sequence analysis. The results revealed two CBG fragments: the authentic amino-terminus of mature human CBG, (Ferlund and Laurell (1981) J. Steroid Biochem. 14:545), together with a second sequence which was identified as starting with residue 342 (Thr) in the mature form of human CBG (Hammond et al. (1987) Proc. Natl. Acad. Sci. USA 84:5153).

The steroid binding properties of human CBG were also tested using a cortisol binding capacity assay (Hammond and Lahteenmaki (1982) Clin. Chem. Acta 132:101) before and after a standard incubation with elastase, as described above. In this way it could be shown that >95% of the steroid binding activity of human CBG was lost after treatment with elastase, indicating that CBG had lost its binding affinity for the anti-inflammatory agent cortisol following exposure to elastase.

I claim:

1. A pharmaceutical composition useful in treating inflammation in a mammal, said composition comprising human CBG, an anti-inflammatory agent which binds therewith, and a pharmaceutically acceptable carrier, wherein the amount of the anit-inflammatory agent represents a molar excess relative to human CBG present in the composition and is sufficient to bind substantially all of the human CBG in the composition.

2. The composition according to claim 1, wherein said anti-inflammatory agent is a glucocorticoid.

3. The composition according to claim 2, wherein said glucocorticoid is selected from prednisolone and methylprednisolone.

4. The composition according to claim 2 which is an injectable solution.

5. The composition according to claim 2 in a form suitable for topical administration.

6. The composition according to claim 2 which is an aerosol.

7. A method for treating inflammation in a mammal, comprising the step of administering to said mammal a pharmaceutical composition comprising CBG, an anti-inflammatory agent which binds therewith, and a pharmaceutically acceptable carrier, wherein the amount of the anti-inflammatory agent represents a molar excess relative to human CBG present in the composition.

8. The method according to claim 7 wherein said anti-inflammatory agent is a glucocorticoid.

9. The method according to claim 8, wherein said anti-inflammatory agent is selected from prednisolone and methylprednisolone.

10. The method according to claim 8, wherein said composition is administered by injection.

11. The method according to claim 8 wherein said composition is administered topically.

12. The method according to claim 8, wherein said composition is administered by inhalation.

13. The composition according to claim 2, wherein the anti-inflammatory agent is cortisol.

14. The composition according to claim 5, wherein the carrier is a cream, lotion or ointment.

15. The composition according to claim 14, wherein the carrier comprises a triglyceride base and a surface active agent.

16. The composition according to claim 6, wherein the carrier comprises a liquid vehicle and a propellant.

17. The method according to claim 8, wherein said anti-inflammatory agent is cortisol.

18. A pharmaceutical composition useful in treating inflammation in a mammal, said composition comprising a CBG, an anti-inflammatory agent which binds therewith, and a pharmaceutically acceptable carrier selected from a composition for topical application and an aerosol inhalable formulation, wherein the amount of the anti-inflammatory agent represents a molar excess relative to the CBG present in the composition and is sufficient to bind substantially all of the CBG in the composition.

19. The composition according to claim 18, wherein the anti-inflammatory agent is a glucocorticoid.

20. The composition according to claim 19, wherein the anti-inflammatory agent is selected from prednisolone and methylprednisolone.

21. The composition according to claim 19, wherein the anti-inflammatory agent is cortisol.

22. The composition according to claim 19 which is an injectable solution.

23. The composition according to claim 19 in a form suitable for topical administration.

24. The composition according to claim 23, wherein the carrier is a cream, lotion or ointment.

25. The composition according to claim 24, wherein the carrier comprises a triglyceride base and a surface active agent.

26. The composition according to claim 19 which is an aerosol.

27. The composition according to claim 26, wherein the carrier comprises a liquid vehicle and a propellant.

28. A pharmaceutical composition useful in treating inflammation in a mammal, said composition comprising a CBG, an anti-inflammatory agent which binds therewith, and a pharmaceutically acceptable carrier, wherein the amount of the anti-inflammatory agent represents a molar excess relative to the CBG present in the composition.

29. The composition according to claim 28, wherein the anti-inflammatory agent is a glucocorticoid.

30. The composition according to claim 29, wherein the anti-inflammatory agent is selected from prednisolone and methylprednisolone.

31. The composition according to claim 29, wherein the anti-inflammatory agent is cortisol.

32. The composition according to claim 29 which is an injectable solution.

33. The composition according to claim 29 in a form suitable for topical administration.

34. The composition according to claim 33, wherein the carrier is a cream, lotion or ointment.

35. The composition according to claim 34, wherein the carrier comprises a triglyceride base and a surface active agent.

36. The composition according to claim 29 which is an aerosol.

37. The composition according to claim 36, wherein the carrier comprises a liquid vehicle and a propellant.

* * * * *